United States Patent [19]
Peters

[11] Patent Number: 5,472,428
[45] Date of Patent: Dec. 5, 1995

[54] METHOD OF USING AN INTUBATION INSTRUMENT

[76] Inventor: Michael J. Peters, 2196 Wycliffe, W. Bloomfield, Mich. 48323

[21] Appl. No.: 215,486
[22] Filed: Mar. 21, 1994
[51] Int. Cl.$^6$ ....................................................... A61M 5/00
[52] U.S. Cl. ............................................. 604/171; 604/271
[58] Field of Search ................................... 604/164, 171, 604/264, 271, 280

[56] References Cited

FOREIGN PATENT DOCUMENTS 2420351  11/1979  France ................................. 604/271

Primary Examiner—Corrine M. Maglione
Attorney, Agent, or Firm—Lyman R. Lyon

[57] ABSTRACT

An intubation instrument has an abraded and adsorbent sheath that is telescoped both internally and externally of a tube. The sheath is provided with a handle to facilitate retraction thereof as the tube is inserted into a body cavity, thereby minimizing transportation of pathogens into the body.

1 Claim, 2 Drawing Sheets

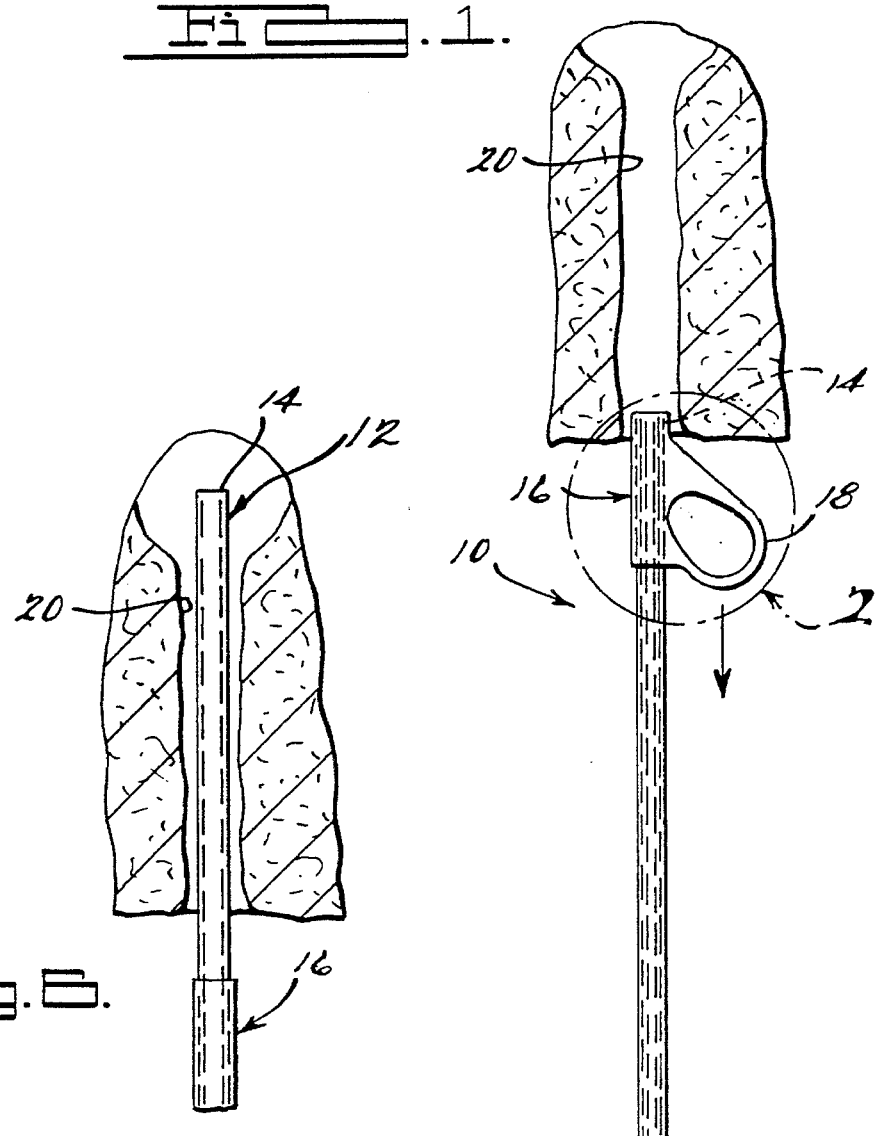
FIG. 1.
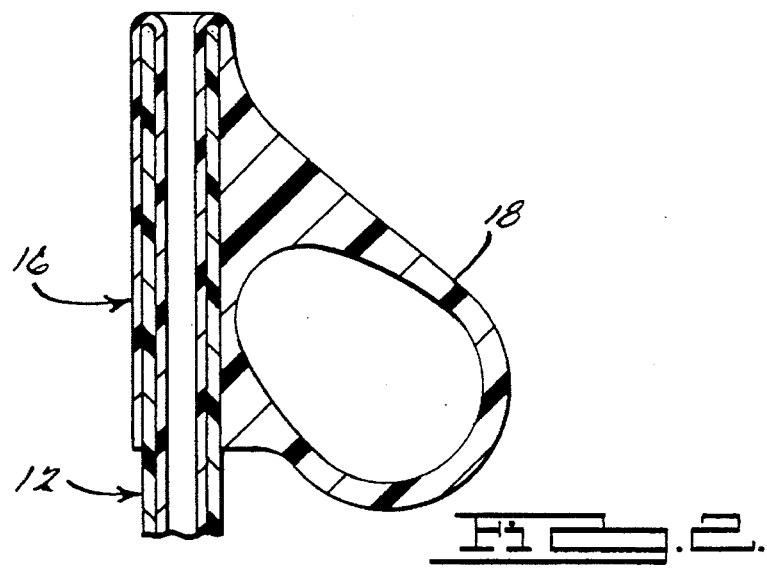
FIG. 2.
FIG. 3.

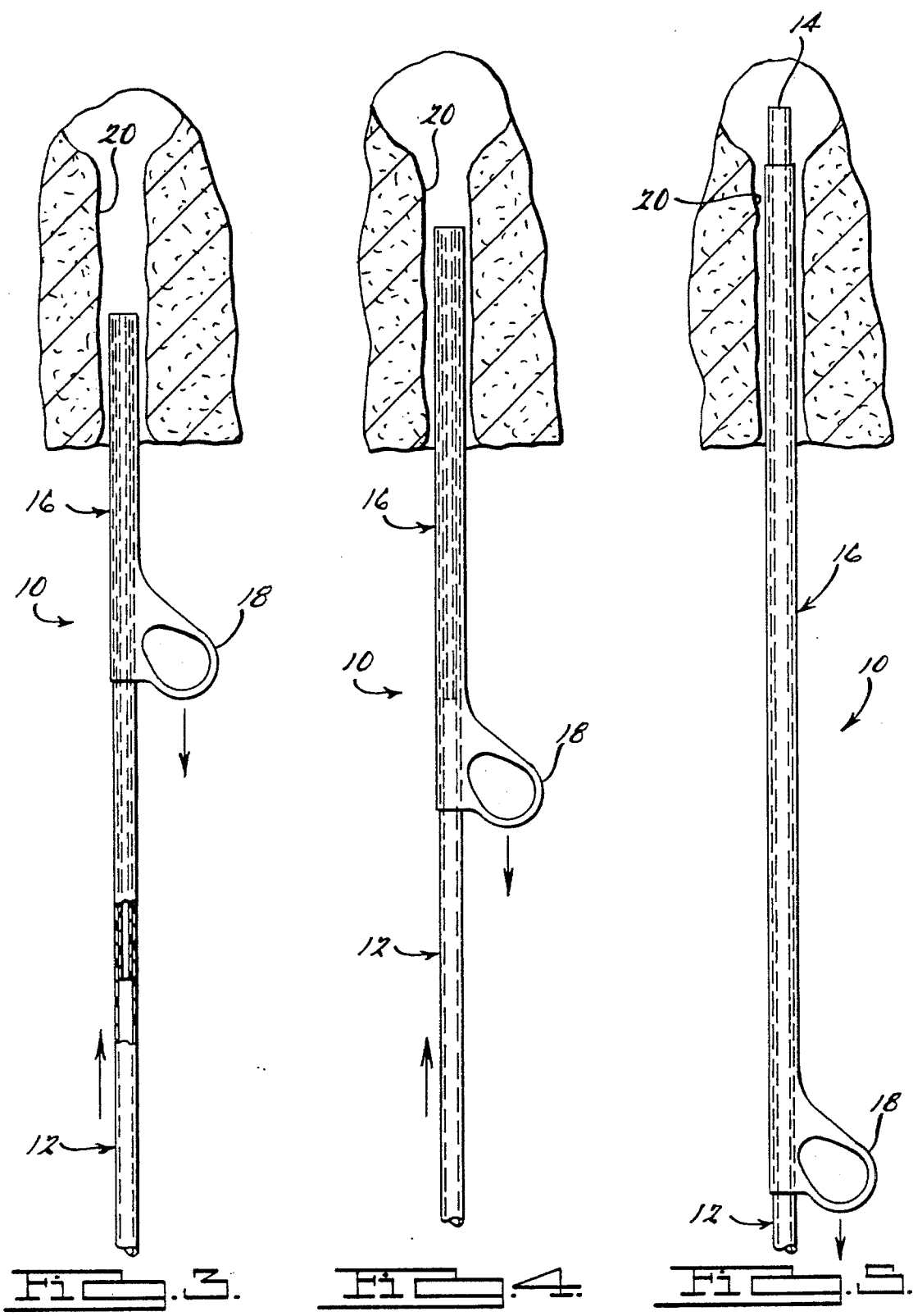

METHOD OF USING AN INTUBATION INSTRUMENT

BACKGROUND OF THE INVENTION

The present invention relates generally to medical devices, and more particularly to an intubation instrument that utilizes a protective sheath disposed about a tube for preventing infection as the tube passes through a body passage.

Intubation devices are often inserted through a bacterially contaminated body passage before terminating in a naturally sterile milieu. Such intubation devices inherently transfer pathogens, such as bacteria, from the contaminated passage into the sterile milieu during the insertion process, thereby increasing susceptibility to infection.

One example of a well known intubation instrument is a bladder catheter, which is a long tubular device that is inserted into the urethra and passed into the bladder to effect the evacuation of urine from the bladder. Urinary tract infections are often induced upon insertion of a conventional bladder catheter, by the transport of bacteria-laden urethral mucus from the distal urethra and external genitalia into the bladder.

Reducing the occurrence of infection caused by intubation devices, for example, bladder catheters, has heretofore been difficult and ineffective. One known arrangement described in U.S. Pat. No. 3,421,509, provides for the insertion of a short protective sleeve into an outer extremity of the urethra before the bladder catheter itself is inserted. Subsequently, the catheter is inserted through the urethra and sleeve, thereby attempting to avoid contact with the contaminated area of the urethra. However, because the urethra is a collapsible tubular membrane, utilization of such a protective sleeve is ineffective because placement of the sleeve in the urethra carries bacterially contaminated mucus further into the urethra. Thus, the use of a protective sleeve is ineffective because even though the catheter initially passes through the sleeve the catheter eventually contacts an accumulation of bacterially contaminated mucus on the internally disposed end of the sleeve. In addition, the protective sleeve merely attempts to avoid contact with, while not removing, any of the harmful contaminated mucus and therefore a significant risk of infection is still present.

U.S. Pat. No, 3,084,693, discloses a catheter that utilizes a membrane having a ring shaped "peripheral stop" at one end. It is also exemplary of an ineffective prior attempt to reduce the onset of infection caused by intubation devices. The "peripheral stop" is retained by the external genitalia thereby causing the membrane to unroll during subsequent insertion of the catheter, in an attempt to create a sterile surface as the catheter advances internally thereof. Unfortunately, the membrane is positioned in a static manner relative to the urethra and disadvantageously remains static therein as the catheter advances. The static nature of the membrane having a "peripheral stop" is undesirable because the bacterially contaminated mucus remains in the urethra and hence a significant risk of infection is still present because the mucus is not transported away from the urethra.

SUMMARY OF THE INVENTION

The aforementioned problems are solved, in accordance with a preferred constructed embodiment of the present invention, by an intubation instrument, for example, a bladder catheter, having an abraded adsorbent sheath that is telescoped both internally and externally of the catheter. The external portion of the sheath is provided with a handle to facilitate retraction thereof relative to the body passage during insertion of the catheter. Because the sheath is drawn out of the bacterially-contaminated passage concomitantly with advancement of the catheter thereinto, bacteria-laden mucus adhering to the abraded adsorbent surface of the sheath is removed from the urethra.

In operation, the operator grips the handle of the sheath and effects a continuous outward displacement of the sheath consistent with the rate of insertion of the catheter so as to maintain constant relative movement between the sheath and the body passage of the patient.

The preferred embodiment uses a sheath which is finely abraded so as to maximize its adsorbent characteristic to aid in the removal of bacterially-contaminated mucus from the urethra.

BRIEF DESCRIPTION OF THE DRAWINGS

FIG. 1 illustrates a preferred embodiment of an intubation instrument prior to insertion into a body passage;

FIG. 2 is an enlarged view, partially in cross section, taken within the circle "2" of FIG. 1; and FIGS. 3–6 are a sequence of illustrations showing the sheath, tube, and body passage of FIG. 1 wherein the sheath is retracted from the body passage as the catheter is concomitantly inserted through the body passage.

DETAILED DESCRIPTION OF THE PREFERRED EMBODIMENT(S)

Referring to the figures, an intubation instrument 10, in accordance with a preferred constructed embodiment of the present invention, comprises a bladder catheter 12 having an insertion end 14. As shown in FIG. 1, a major portion of a protective sheath 16 is initially disposed internally of the catheter 12. An end portion of the sheath 16 is reentrantly folded about the insertion end 14 of the catheter 12.

The sheath 16 is made of flexible, fluid impervious material, for example, a thin, abraded, adsorbent latex membrane so disposed as to present the adsorbent, abraded surface to the walls of the body cavity upon retraction of the sheath 16.

In accordance with the present invention, and as best seen in FIGS. 2, the sheath 16 is provided with a handle 18 which facilitates retraction thereof. The handle 18 of the sheath 16 is preferably integrally formed with the sheath 16 and is positioned proximate to the insertion end 14 of the tube 12. The remaining portion of the sheath 16 is telescoped internally of the tube 12.

As seen in FIGS. 3–5, the sheath 16 is retracted outwardly from a body passage 20 concomitantly with insertion of the tube 12 inwardly into the body passage 20. In operation, a medical practitioner, grips the handle 18 of the sheath 16 and effects a continuous outward displacement of the sheath 16 relative to the body passage 20 in excess of the rate of insertion of the tube 12 inwardly into the body passage 20 thereby to maintain constant relative movement between the sheath 16 and the body passage 20 of the patient. Because the sheath 16 is retracted from the body passage 20 concomitantly with insertion of the tube 12 thereinto, pathogens, such as bacteria-laden mucus, are removed because the mucus adheres to the abraded adsorbent surface of the sheath 16. The catheter 10 of the present invention not only prevents the tube 12 from contacting various pathogens, but also advantageously removes pathogens from the body passage 20 so as to minimize transportation of bacteria into the body. As seen in FIG. 6, the entire sheath 16 is retracted from the body passage 20.

While the preferred embodiment of the invention has been disclosed, it should be appreciated that the invention is susceptible of modification without departing from the scope of the following claims.

I claim:

1. A method of ventilating a body cavity comprising the steps of:

providing a tube having an insertion end;

providing said tube with a removable protective sheath with a major portion of said sheath disposed internally of said tube and an end portion of said sheath reentrantly folded about the insertion end of said tube;

providing the end portion of said sheath with a gripping means;

inserting the insertion end of said tube and reentrantly folded portion of said sheath into said body cavity;

retracting said gripping means away from said body cavity to effect withdrawal of the sheath outwardly of said cavity; and advancing said tube inwardly of said body cavity concomitantly with retraction of said sheath.

* * * * *